(12) United States Patent
Galm et al.

(10) Patent No.: US 9,370,386 B2
(45) Date of Patent: Jun. 21, 2016

(54) PLATING CONCEPT FOR DISTAL RADIAL FRACTURES

(75) Inventors: Andre Galm, Solothurn (CH); Martin Langer, Unna (DE); Dirk Kerstan, Solothurn (CH); Christof Dutoit, Solothurn (CH); Franco Cicoira, Bettlach (CH); Mirko Rocci, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1125 days.

(21) Appl. No.: 12/952,756

(22) Filed: Nov. 23, 2010

(65) Prior Publication Data
US 2011/0218576 A1 Sep. 8, 2011

Related U.S. Application Data

(60) Provisional application No. 61/264,745, filed on Nov. 27, 2009.

(51) Int. Cl.
*A61B 17/80* (2006.01)
*A61B 17/17* (2006.01)

(52) U.S. Cl.
CPC ........... *A61B 17/8061* (2013.01); *A61B 17/808* (2013.01); *A61B 17/1728* (2013.01); *A61B 2017/1782* (2013.01)

(58) Field of Classification Search
USPC ........ 606/70, 71, 86 R, 96, 98, 280–286, 289
See application file for complete search history.

(56) References Cited

U.S. PATENT DOCUMENTS

| 5,197,966 | A | 3/1993 | Sommerkamp | |
|---|---|---|---|---|
| D458,374 | S | 6/2002 | Btyant et al. | |
| 6,719,759 | B2 * | 4/2004 | Wagner et al. | 606/282 |
| 6,866,665 | B2 | 3/2005 | Orbay | |
| 2001/0011172 | A1 * | 8/2001 | Orbay et al. | 606/69 |
| 2002/0143338 | A1 | 10/2002 | Orbay et al. | |
| 2004/0102778 | A1 | 5/2004 | Huebner et al. | |
| 2004/0102788 | A1 * | 5/2004 | Huebner et al. | 606/96 |
| 2004/0260291 | A1 | 12/2004 | Jensen | |
| 2005/0004574 | A1 | 1/2005 | Muckter | |
| 2005/0065524 | A1 | 3/2005 | Orbay | |

(Continued)

FOREIGN PATENT DOCUMENTS

| CN | 2390564 | 8/2000 |
|---|---|---|
| CN | 2402279 | 10/2000 |

(Continued)

*Primary Examiner* — Christian Sevilla
(74) *Attorney, Agent, or Firm* — Fay Kaplun & Marcin, LLP

(57) ABSTRACT

A bone fixation plate comprises a plate body extending from a first end configured for placement over a shaft of a bone to a second end configured and dimensioned for placement over an epiphysis of the bone, an outer diameter of the plate body increasing from the first end to the second end to substantially conform to dimensions of the bone. An opening extends through the plate from a first surface which faces away from the bone when mounted thereonto to a second surface which faces the bone when in the desired orientation, the opening being positioned so that, when mounted over the bone, a fracture of the bone is visible therethrough to aid in alignment of the bone plate. First and second holes extend through the plate, each of the first and second holes being structured to lockingly engage a threaded head of a bone fixation device inserted thereinto.

22 Claims, 11 Drawing Sheets

(56) References Cited

U.S. PATENT DOCUMENTS

| | | | |
|---|---|---|---|
| 2005/0075641 A1 | 4/2005 | Singhatat et al. | |
| 2005/0153073 A1 | 7/2005 | Zheng et al. | |
| 2005/0171544 A1 | 8/2005 | Falkner, Jr. | |
| 2006/0173458 A1 | 8/2006 | Forstein et al. | |
| 2006/0235405 A1* | 10/2006 | Hawkes | 606/69 |
| 2006/0259039 A1 | 11/2006 | Pitkanen et al. | |
| 2007/0123881 A1* | 5/2007 | Ralph et al. | 606/69 |
| 2007/0123886 A1 | 5/2007 | Meyer et al. | |
| 2007/0162018 A1 | 7/2007 | Jensen et al. | |
| 2007/0239168 A1 | 10/2007 | Kuenzi et al. | |
| 2008/0140127 A1* | 6/2008 | Vasta et al. | 606/280 |
| 2008/0300637 A1 | 12/2008 | Austin et al. | |

FOREIGN PATENT DOCUMENTS

| | | |
|---|---|---|
| CN | 1748655 | 3/2006 |
| CN | 101536928 | 9/2009 |
| CN | 201308534 | 9/2009 |
| DE | 10125092 | 12/2001 |
| EP | 1132052 | 9/2001 |
| JP | 2004-223042 | 8/2004 |
| JP | 2004-313514 | 11/2004 |
| JP | 2006-087330 | 4/2006 |
| JP | 3141392 | 4/2008 |
| JP | 2008-272485 | 11/2008 |
| WO | 96/22743 | 8/1996 |
| WO | 96/25118 | 8/1996 |
| WO | 01/56452 | 8/2001 |
| WO | 2004/086990 | 10/2004 |
| WO | 2004/089233 | 10/2004 |
| WO | 2005/034780 | 4/2005 |
| WO | 2005/037114 | 4/2005 |
| WO | 2005/044122 | 5/2005 |
| WO | 2005/046494 | 5/2005 |
| WO | 2006/014391 | 2/2006 |
| WO | 2006/065512 | 6/2006 |
| WO | 2006/072379 | 7/2006 |
| WO | 2006/099766 | 9/2006 |
| WO | 2006/102081 | 9/2006 |
| WO | 2009/105201 | 8/2009 |

\* cited by examiner

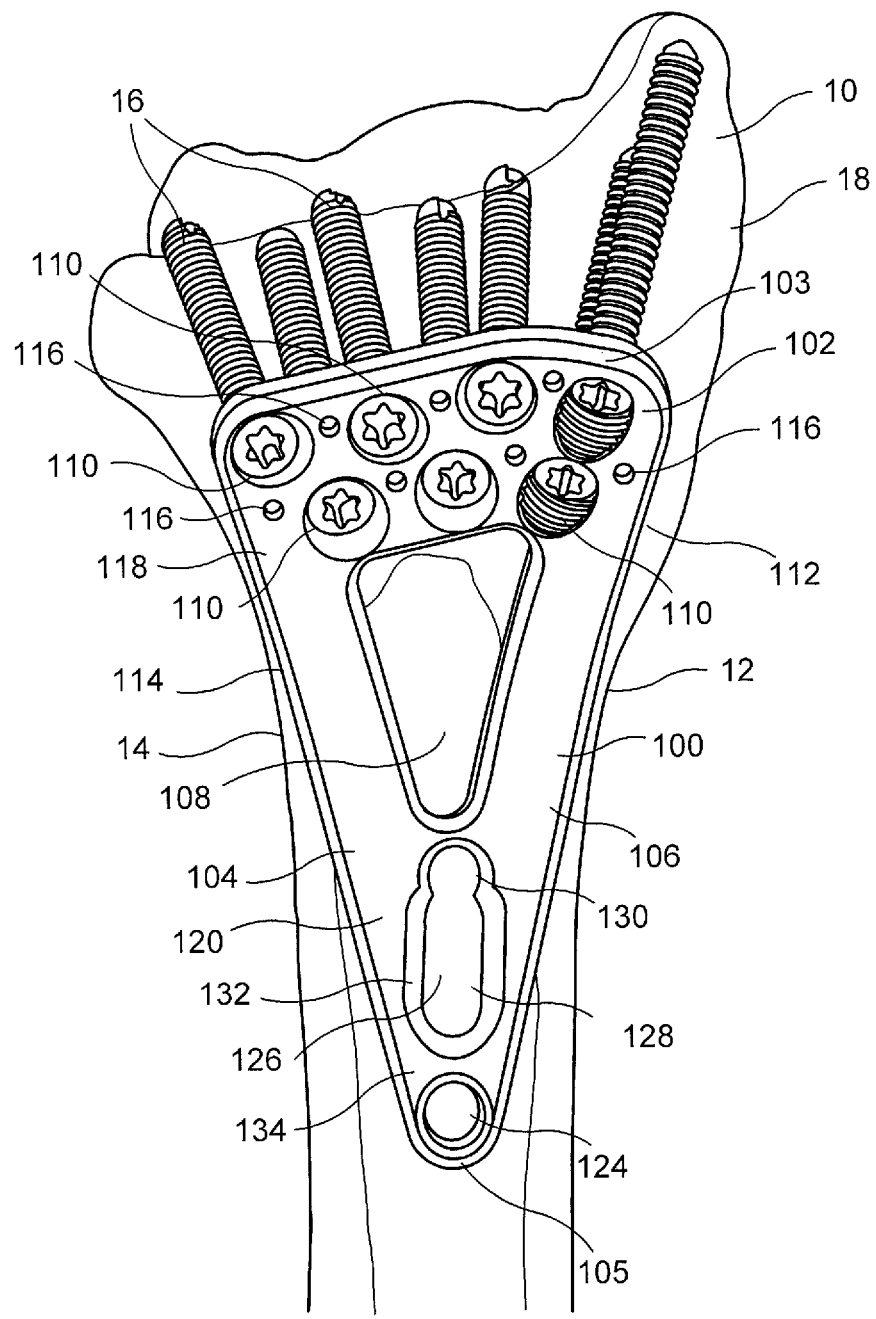
F I G. 1

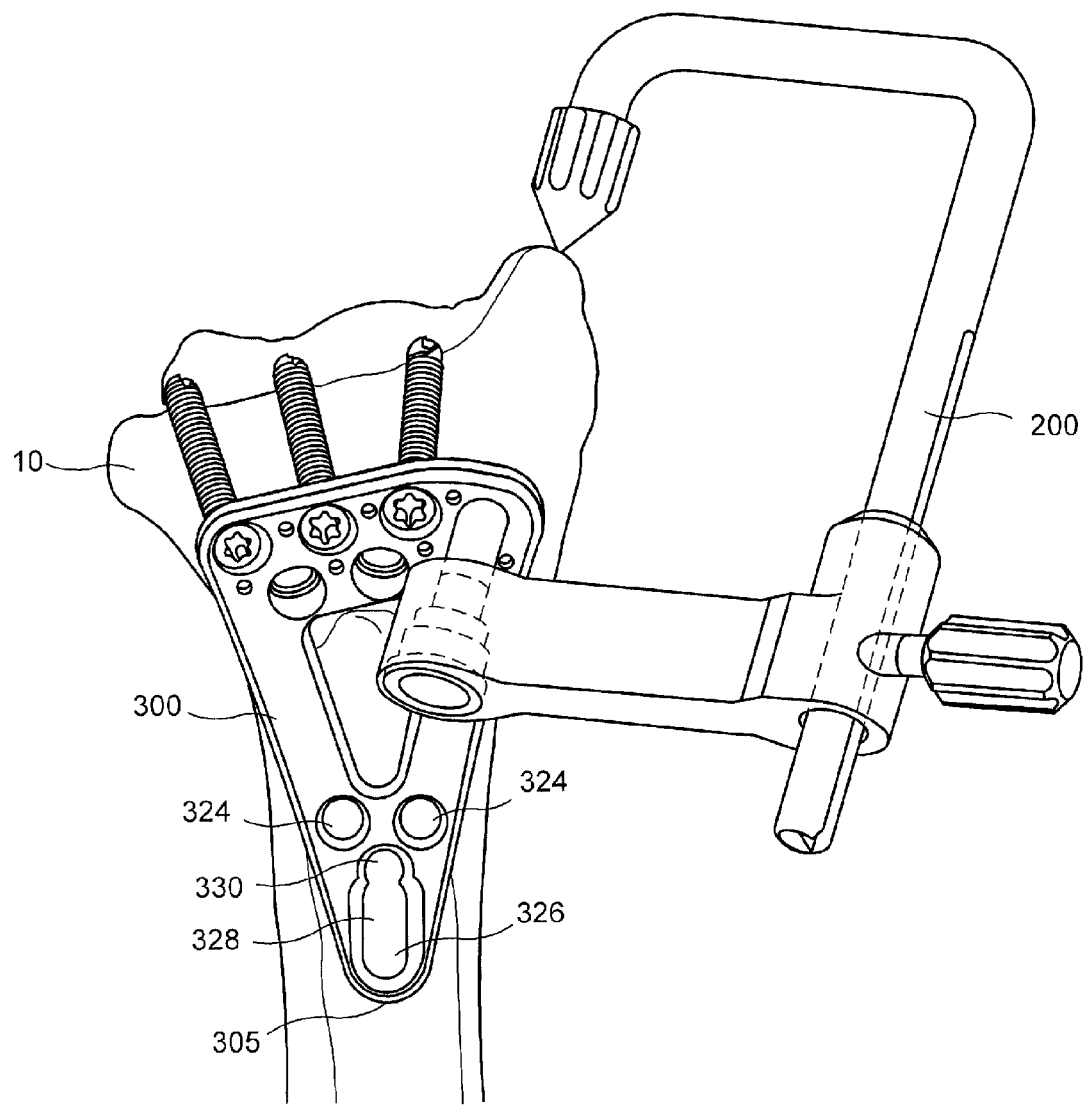
F I G. 5

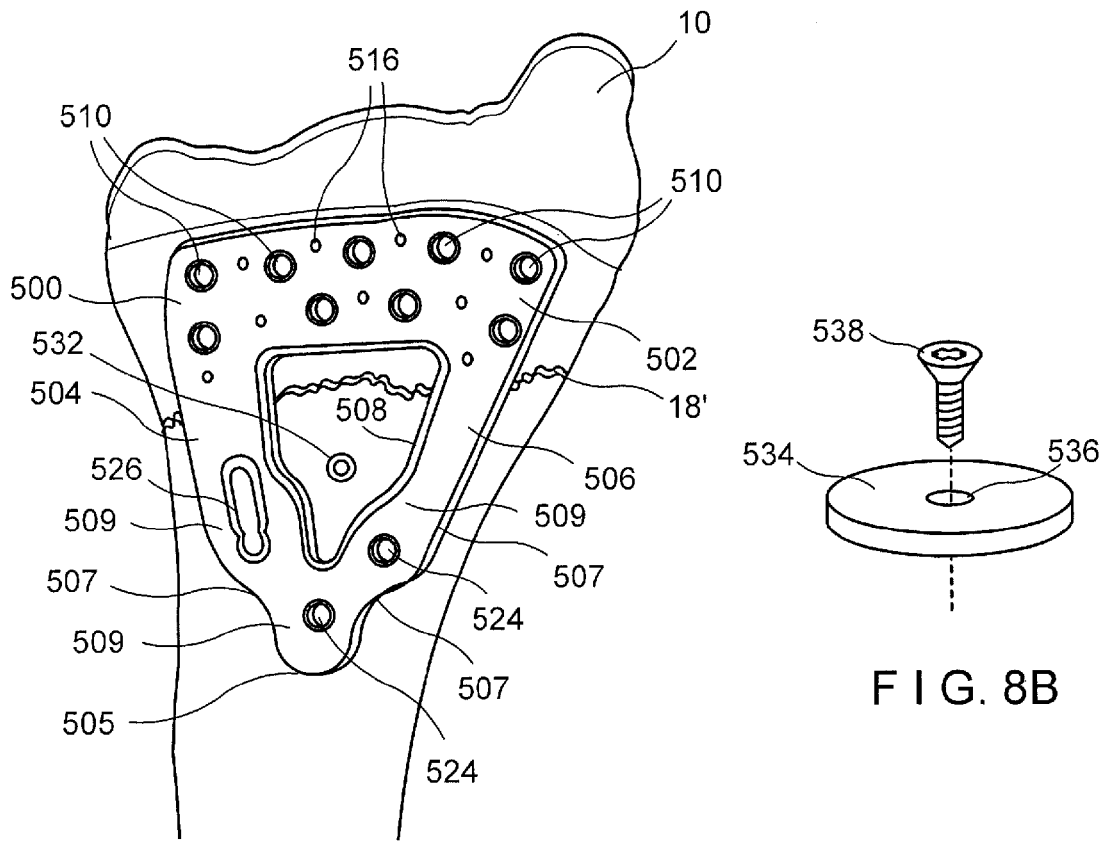
F I G. 8A
F I G. 8B
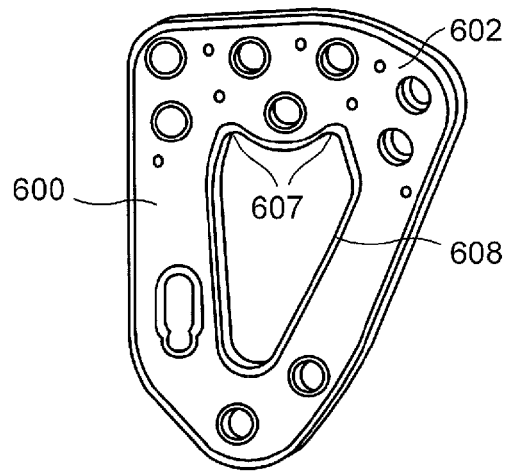
F I G. 9

PLATING CONCEPT FOR DISTAL RADIAL FRACTURES

PRIORITY CLAIM

The present application claims priority to U.S. Provisional Application Ser. No. 61/264,745 entitled "Plating Concept for Distal Radial Fractures" filed on Nov. 27, 2009 to André Galm, Martin Langer, Dirk Kerstan, Christof Dutoit, Franco Cicoira and Mirko Rocci, the entire disclosure of which is incorporated herein by reference.

FIELD OF THE INVENTION

The present invention relates to the field of bone fixation and, more particularly, is related to the fixation of fractures via a bone fixation plate configured and dimensioned to permit the insertion of bone fixation screws therethrough at any of a plurality of angles selected by a physician to conform to the requirements of a target procedure.

BACKGROUND

Procedures for the fixation of intra-articular and extra-articular bone and osteotomies of the distal radius and other smaller bones have often employed variable angle locking screws with bone plates including correspondingly configured variable angle holes. The combination of a variable angle locking screw with a variable angle hole allows a user to select an angulation of the screw (within a permitted range of angulation) relative to an axis of the hole to, for example, increase a holding strength thereof with the bone.

SUMMARY OF THE INVENTION

The present invention is directed to a bone fixation plate comprising a plate body extending from a first end to a second end, the first end being configured and dimensioned for placement over a shaft of a bone, the second end being configured and dimensioned for placement over an epiphysis of the bone, an outer diameter of the plate body increasing from the first end to the second end to substantially conform to dimensions of the bone. An opening extends through the plate from a first surface which, when the plate is mounted on the target bone in a desired orientation, faces away from the bone to a second surface, which when in the desired orientation, faces the bone, the opening being positioned so that, when the plate is mounted over a target portion of the bone, a fracture of the bone is visible therethrough to aid in alignment of the bone plate. First and second holes extend through the plate from the first surface to the second surface, each of the first and second holes being structured to lockingly engage a threaded head of a bone fixation device inserted thereinto.

BRIEF DESCRIPTION OF THE DRAWINGS

FIG. 1 shows a perspective view of a system according to a first exemplary embodiment of the present invention;

FIG. 5 depicts another step of an exemplary method for the fixation of the system of FIG. 1 to the bone;

FIG. 8A depicts a bone plate according to a third alternate embodiment of the present invention;

FIG. 8B depicts a bone fixation element for use with the bone plate of FIG. 8A;

FIG. 9 depicts a bone plate according to a fourth alternate embodiment of the present invention;

DETAILED DESCRIPTION

Figure 2:
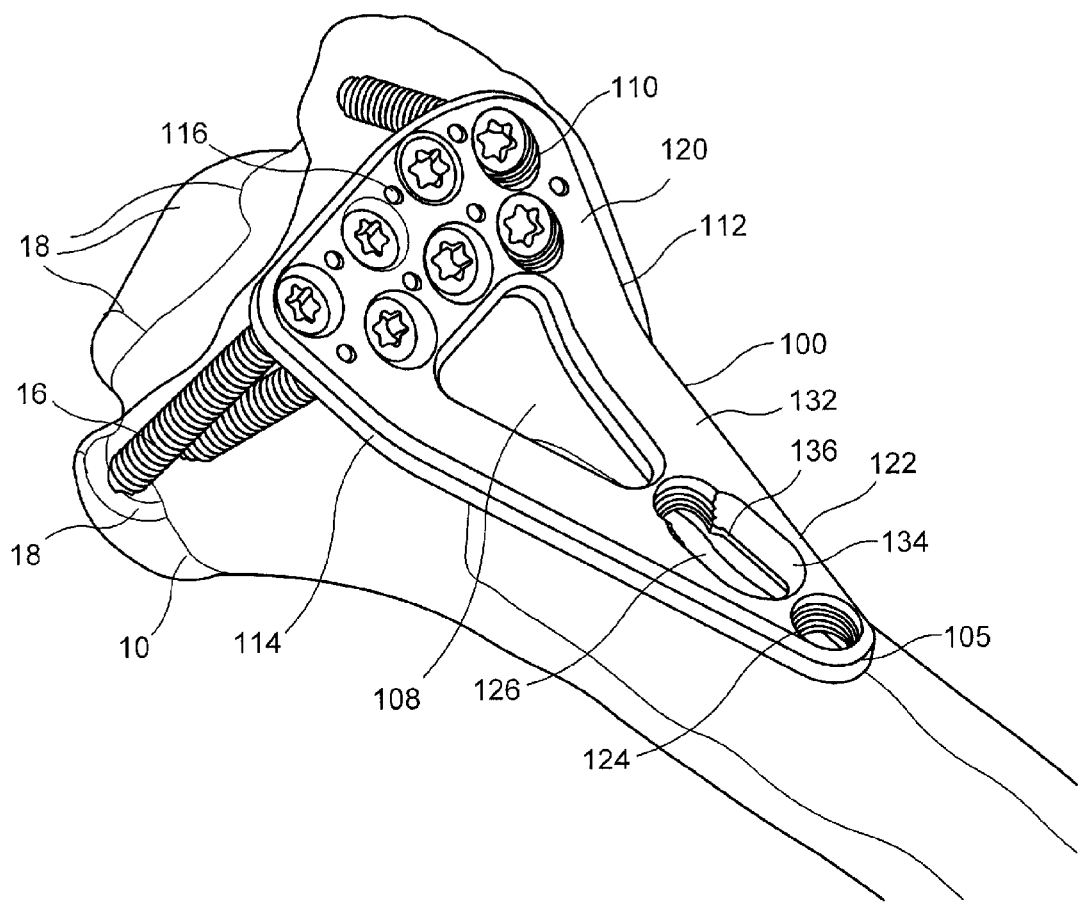
FIG. 2 shows another perspective view of the system of FIG. 1.

The present invention may be further understood with reference to the following description and the appended drawings, wherein like elements are referred to with the same reference numerals. The exemplary embodiments of the present invention relate to a system and method for the fixation of bone fractures of the distal radius and other small bones of a body. The exemplary system and method of the present invention may also be used to strengthen poor quality bone such as, for example, osteoporotic bone. An exemplary bone fixation plate according to the present invention is formed with a substantially triangular profile and comprises a window extending therethrough to aid in positioning of the bone plate over a target portion of a bone. In an exemplary embodiment, the bone plate according to the present invention is generally shaped as an isosceles triangle with a first wall thereof configured to rest substantially perpendicular to a longitudinal axis of the radius while second and third walls thereof extend away from the first wall to converge at an intersection which, when the plate is positioned in a desired location, is located substantially over a longitudinal axis of the radius. The first wall includes a plurality of locking holes extending therethrough to receive fixation elements (e.g., bone screws and/or pins) for securing the bone plate to a condyle of a target radius. In addition, a compression hole and/or a variable angle plate hole is included at the intersection of the second and third walls to secure the bone plate to the shaft of the radius. An exemplary aiming and positioning device according to the present invention permits the placement of the bone plate over a target portion in a manner that achieves bone reduction and intra operative compression while also aiding a physician or other user in determining a proper bone screw length, as will be described in greater detail below. It is noted that although the exemplary system and method of the present invention are described with respect to fixation of the radius and a particular plate geometry suited thereto, the exemplary system and method may also be used for the fixation of any type of bone in the body with any variety of bone plates.

Figure 3:
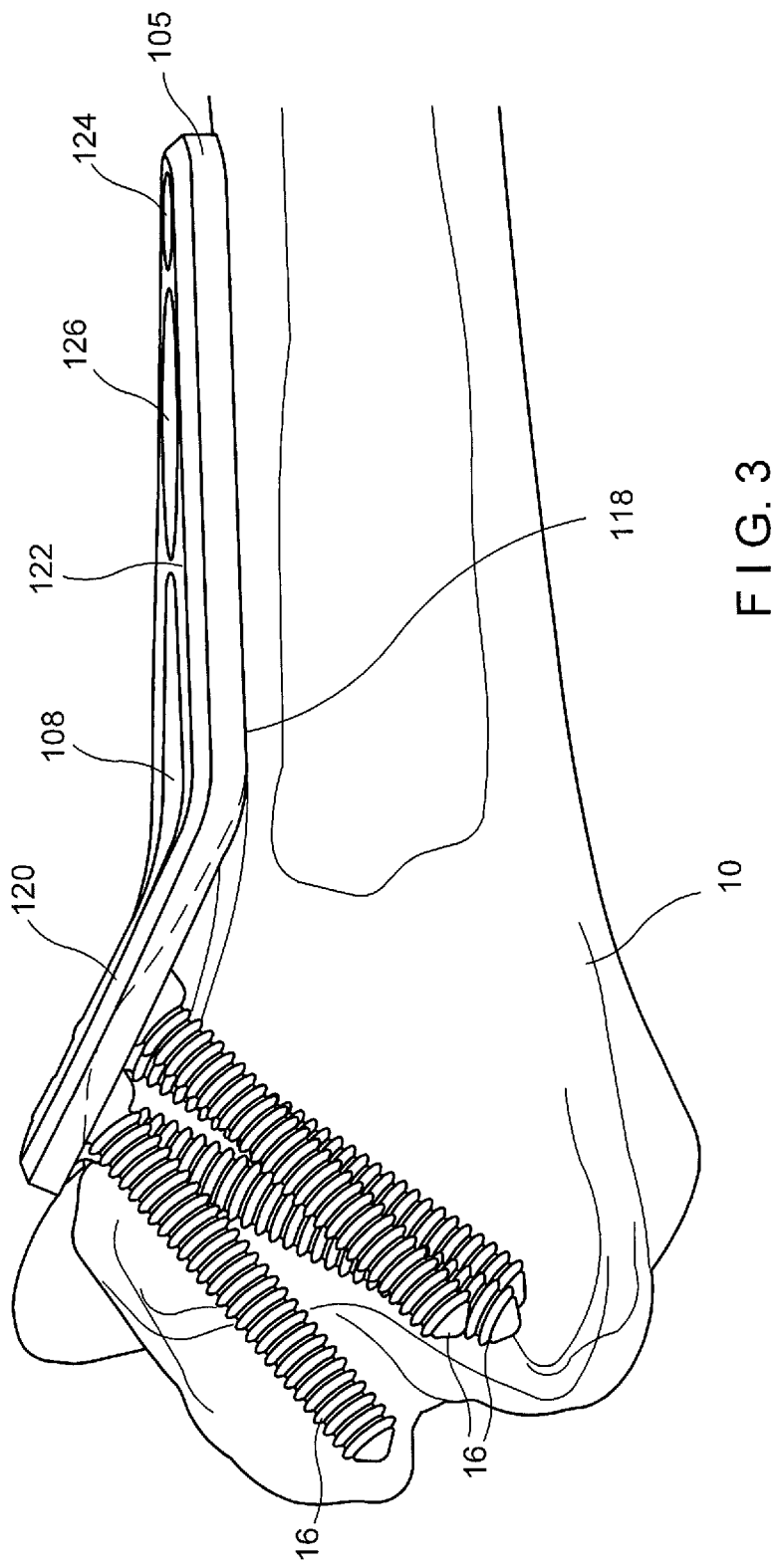
FIG. 3 shows a lateral view of the system of FIG. 1.

As shown in FIGS. 1-3, a bone plate 100 according to a first exemplary embodiment of the present invention comprises a first wall 102 at a first end 103 and second and third walls 104, 106, respectively, converging at a second end 105 so that the bone plate 100 has a substantially triangular outer profile when viewed from above a surface of the bone plate 100 which, when in a desired location on a target bone, faces away from the bone. As would be understood by those skilled in the art, when viewed from a side thereof, the bone plate 100 preferably has a curve corresponding to a shape of the portion of bone to which it is to be secured. It is noted that the angles between each of the first, second, and third walls 102, 104, 106 and the dimensions of each of these walls may be modified as needed to suit the dimensions of a target bone 10, as those skilled in the art will understand. The bone plate 100 of the present invention may be formed, for example, of titanium, stainless steel, polyetheretherketone ("PEEK") or radiolucent PEEK as those skilled in the art will understand. A window 108 having a profile substantially matching the outer profile of the bone plate 100 extends through a center thereof. In an exemplary embodiment, the window 108 is positioned so that a width of each of the second and third walls 104, 106 is substantially the same. The window 108 permits viewing of a bone fracture line therethrough to aid in positioning of the bone plate 100 over a target portion of the bone 10 as would be understood by those skilled in the art. In a preferred embodiment, a width of the first wall 102 is greater than the width of the second and third walls 104,106, so that the first wall 102 can accommodate two substantially parallel lines of screw holes distributed along its length. Specifically, the first wall 102 is configured for placement over a distal portion of the radius 10 (i.e., the portion of the radius adjacent the hand while the proximal portion of the radius is adjacent the elbow) and comprises a set of screw holes 110 extending therethrough, the screw holes 110 all having substantially the same diameter (e.g., 3.5 mm.) or, in another embodiment, having different diameters to permit the insertion of different sized bone screw therethrough. Specifically, in the embodiment of FIGS. 1-3, two rows of screw holes 110 are provided in the first wall 102—a first row adjacent to the first end 103 having four screw holes 110 and a second row of three screw holes 110 each being aligned with a gap between adjacent screw holes 110 of the first row. It is noted, however, that the screw holes 110 in the second row may also be longitudinally aligned with the screw holes 110 of the first row or in any other spatial relation thereto without deviating from the spirit and scope of the present invention.

Each of the screw holes 110 defines an axis angled to guide a bone fixation element (e.g., bone screw 16) therethrough into the bone 10 along a desired axis which preferably does not intersect within the bone with any of the other screw hole axes. In addition, the screw holes 110 are configured so that a bone screw 16 inserted therethrough extends to an extremity of the bone 10 without interfering with any of the other bone screws 16 and without extending through an opposing cortical surface of the bone 10. Specifically, screw holes 110 adjacent to the right and left lateral walls 112, 114 of the bone plate 100 are angled so that bone screws 12 inserted therethrough extend outward toward the respective right and left lateral edges 12, 14 of the bone 10. The screw holes 110 are formed with internal threading configured to permit locking, screwable insertion of the heads of the bone screws 16 therein. Accordingly, the exemplary bone plate 100 of the present invention finds particular utility in bone fractures resulting in two or more bone fragments, as will be described in greater detail with respect to the exemplary method of the present invention. The angles of the screw holes 110 may also be affected by a contour of the bone plate 100. Specifically, as shown in FIG. 3, the bone plate 100 is preferably contoured so that a second surface 118 is seated against the bone in an operative configuration. It is noted that although the exemplary embodiment shown comprises first and second planar portions 120, 122 positioned at a predetermined angle relative to one another, any contouring of the bone plate 100 lies within the scope of the present invention and the contour of the plate 100 may be modified by the user (e.g., surgeon) to more closely match it to the anatomy of the patient.

The first wall 102 also comprises a plurality of Kirschner-wire ("K-wire") holes 116 adjacent to the screw holes 110 configured to permit the insertion of a K-wire (not shown) therethrough to aid in positioning the bone plate 100 over the target portion of bone, as those skilled in the art will understand and as described in greater detail below.

The bone plate 100 also comprises a fixed angle threaded locking hole 124 extending therethrough adjacent to the second end 105. The locking hole 124 may be configured so that a bone screw (not shown) inserted therethrough extends substantially perpendicular to a plane of the second planar portion 122 of the plate 100. The second planar portion 122 also comprises a combination hole 126 having a first substantially elliptical compression hole portion 128 and a second substantially circular threaded portion 130. An axis of the combination hole 126 extends substantially perpendicularly through the bone plate 100 but, as those skilled in the art will understand, may be altered to permit insertion of a bone screw (not shown) therethrough at any desired angle relative to a plane of the second planar portion 122. Specifically, the non-threaded portion 128 comprises a substantially rounded tapered portion 134 extending into the bone plate 100 from a first surface 132 by a predetermined distance and open to a substantially perpendicular portion 136.

Figure 4:
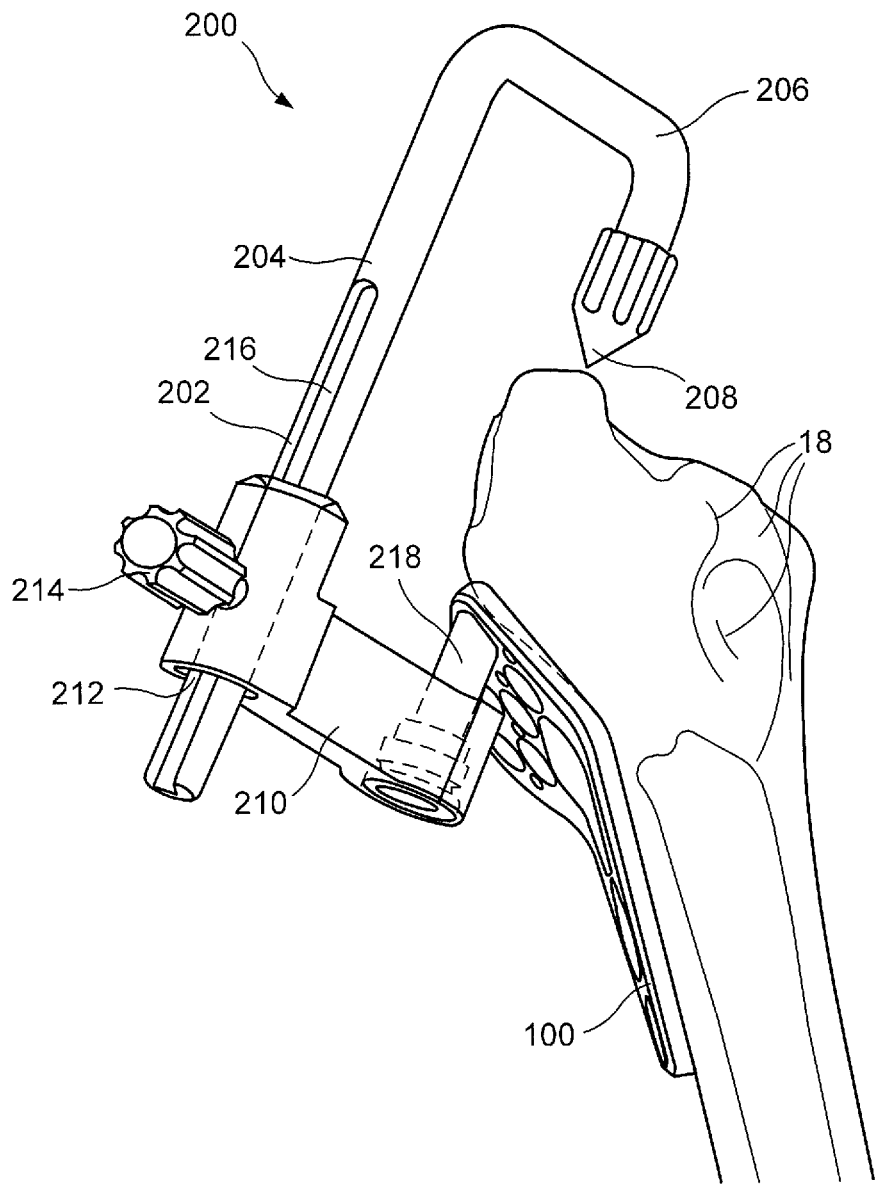
FIG. 4 depicts a first step of an exemplary method for the fixation of the system of FIG. 1 to a bone.

FIGS. 4-5 depict an exemplary method according to the present invention. In a first step, an incision is made through a portion of skin adjacent to the site of a fracture 18. The bone plate 100 is then positioned over the bone 10 so that the first wall 102 is located over a distal radius fracture site. Specifically, the plate 100 is positioned using an aiming device 200 comprising a substantially cylindrical hooked arm 202, a longitudinal section 204 and a hooked section 206 with a pointed tip 208. A handle 210 over the arm 202 includes a through-hole 212 configured to slidably receive the arm 202 therethrough and a tightening mechanism 214 to lock the position of the handle 210 relative to the arm 202. The cross-sectional shape and size of the through-hole 212 is substantially similar to a cross-sectional shape and size of a portion of the arm 202 comprising a track 216 defined as a cut-out on the arm 202. The handle 210 is slidable along the track 216 and is prevented from sliding over outlying portions of the arm 202 due to the increase in diameter at these portions. As those skilled in the art will understand, the location and dimensions of the track 216 prevent rotation of the handle 210 relative to the arm 202. If such a rotation is desired, however, the track 216 may be replaced with a substantially cylindrical reduced diameter portion of the arm 202. A free end of the handle 210 comprises a substantially cylindrical pin 218 having approximately the same diameter as the screw holes 110 of the bone plate 100. Accordingly, the pin 218 may be at least partially inserted into the screw holes 110 to aid in positioning of the bone plate 100 over the bone 10. The aiming device 100 is positioned so that the pointed tip 208 is seated over an approximated midpoint of a radial styloid of the radius 10 and so that the pin 218 is positioned through a screw hole 110 located closest to the right lateral wall 112. In this position, the bone plate 100 is seated proximate to the Watershed Line of the radius 10 to prevent complications with sinews of the body, as those skilled in the art will understand. K-wires may be inserted through the K-wire holes 116 to aid in positioning and temporarily maintaining a position of the bone plate 100 over the bone 10.

The bone screws 16 are then screwed into the screw holes 110, excluding the screw hole 110 engaging the pin 218. It is noted that although seven plate holes 110 are depicted in the bone plate 100, a physician or other user may choose to insert bone screws 16 through all or only a select number of the screw holes 110—e.g., as required by the location and number of fragments of the bone 10. Furthermore, as those skilled in the art will understand, aiming blocks may be used to aid in insertion of the bone screws through the bone plate 100 and into the bone 10. Bone screws may also be inserted through one or both of the locking hole 124 and the combination hole 126 either prior to or after the removal of the aiming arm 200 from the bone 10. As those skilled in the art will understand, a bone screw (not shown) may be inserted through the non-threaded portion 128 of the combination hole at any desired angle or may be inserted through the threaded portion 130 at an angle substantially perpendicular to a plane housing the second planar portion 122. The exemplary system and method of the present invention permits the use of fixed angle locking screws in the bone plate 100 while still permitting an optimal placement of bone screw 16 in the radial styloid of the radius 10. Furthermore, the extraarticular bone fixation procedure according to the present invention permit the placement of the bone plate 100 close to the articular joint of the radius 10 while preventing problems with sinews as commonly experienced with presently available bone fixation devices.

Figure 6:
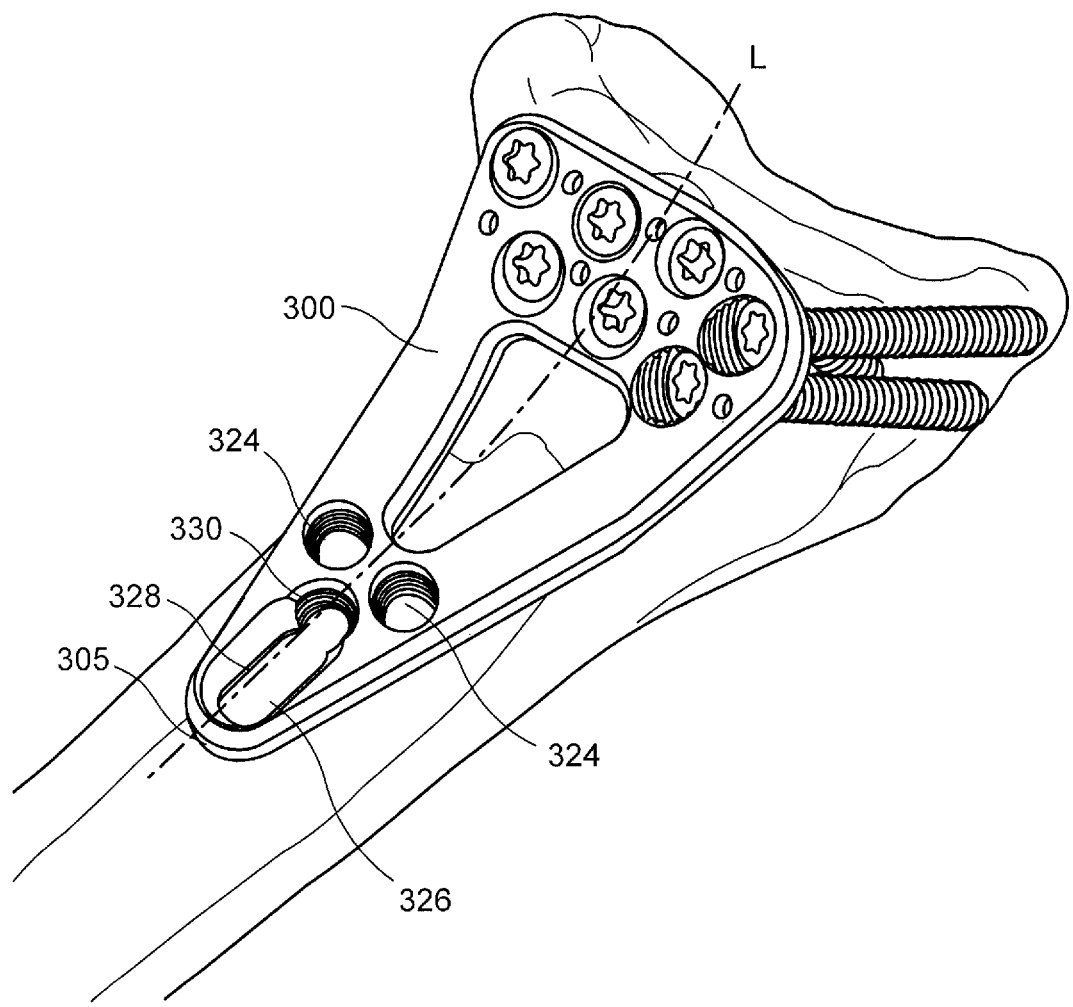
FIG. 6 depicts a bone plate according to a first alternate embodiment of the present invention.

As shown in FIGS. 5-6, a bone plate 300 according to a first alternate embodiment of the present invention, is substantially similar to the bone plate 100 of FIGS. 1-3 except for the arrangement of the holes extending through a second end 305 thereof. Specifically, whereas the bone plate 100 comprises one locking hole 124 at the second end 105, the bone plate 300 comprises a combination hole 326 at the second end 305 and a pair of threaded locking holes 324 separated from the second end 305 by a predetermined distance. The combination hole 326 is formed substantially similarly to the combination hole 126 of FIGS. 1-3, having a non-threaded elliptical section 328 and a threaded section 330. Like the bone plate 100, the bone plate 300 is substantially symmetrical across a longitudinal centerline L, the locking holes 324 and combination hole 326 being symmetrically disposed on the bone plate 300.

Figure 7:
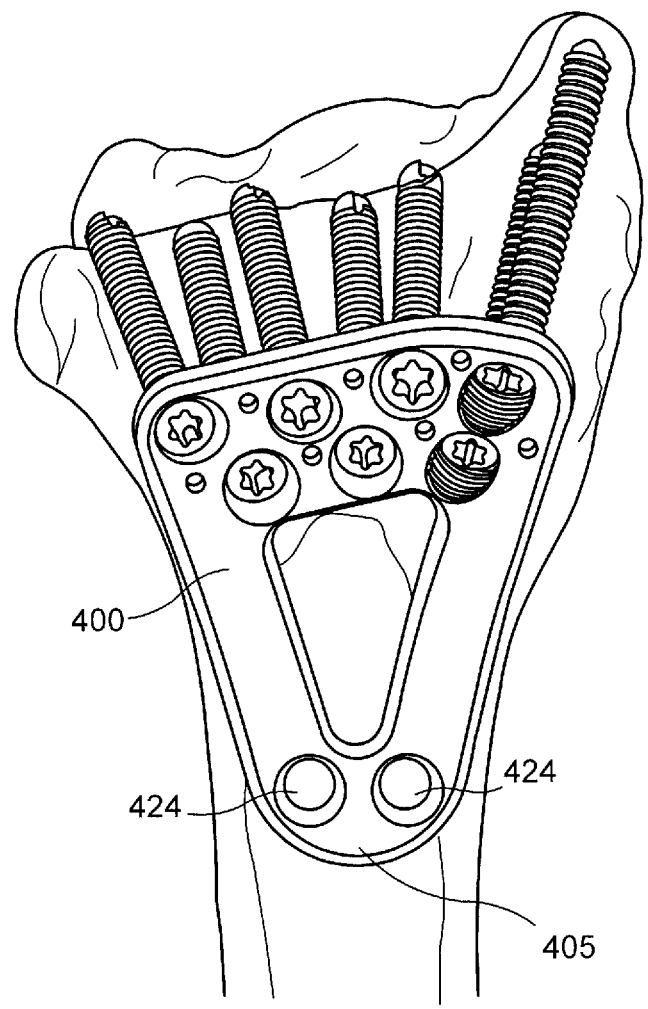
FIG. 7 depicts a bone plate according to a second alternate embodiment of the present invention.

As shown in FIG. 7, a bone plate 400 according to a second alternate embodiment of the present invention is substantially similar to the bone plate 300 except that the second end 405 thereof does not include a combination hole. Rather, the bone plate 400 comprises only two threaded locking holes 424 symmetrically disposed at a location adjacent the second end 405, the threaded locking holes extending substantially perpendicularly to a plane housing the bone plate 400, as described in greater detail in earlier embodiments.

As shown in FIGS. 8A-8B, a bone plate 500 according to a third alternate embodiment of the present invention is substantially similar to the bone plate 100 of FIGS. 1-3 but comprises nine screw holes 510 disposed on a first wall 502 in a distribution pattern substantially similar to the distribution pattern of the screw holes 110 of the bone plate 100. Portions of the second and third walls 504, 506 adjacent to a second end 505 of the bone plate 500 are provided with a plurality of indentations 507 defining a plurality of increased width portions 509 housing threaded locking holes 524 and a combination hole 526 substantially similar to the threaded locking hole 124 and the combination hole 126. The combination hole 526 may be provided on the second wall 504 and the locking holes 526 on the third wall 506 and adjacent the second end 505, although any variation of these positions is also envisioned. The exemplary bone plate 500 is used for the fixation of a fracture 18' of a radius in the same manner described above.

An exemplary method of use of the bone plate 500 is substantially similar to the method discussed above with respect to the bone plate 100. However, due to the location of the fracture being medial of the first wall 502, an additional strengthening means may be employed with the bone plate 500. Specifically, a guide hole 532 may be drilled through a portion of the bone 10 positioned through a window 508. A washer 534 may then be positioned over the guide hole 532 so that an opening 534 of the washer is aligned with the guide hole. A bone screw 536 may then be used to secure the washer to the bone 10. In an exemplary embodiment, the washer 534 may be smaller than the window 508 so that the washer 534 does not interfere with the bone plate 500. The washer 534 may be formed of the same material as the bone plate 500 or may be formed of another material known in the art.

As shown in FIG. 9, a bone plate 600 according to yet another embodiment of the present invention is substantially similar to the bone plate 500 except that an outer profile of the bone plate 600 and a window 608 are shaped differently. Specifically, an outer profile of the bone plate 600 may be substantially similar to the outer profile of the bone plate 100 while the window 608 is formed as an oblong shape having two indentations 607 extending into a first wall 602. The indentations 607 may permit the insertion of a bone screw (not shown) adjacent the first wall 602 or may serve to increase visibility of a fracture site therethrough.

Figure 10:
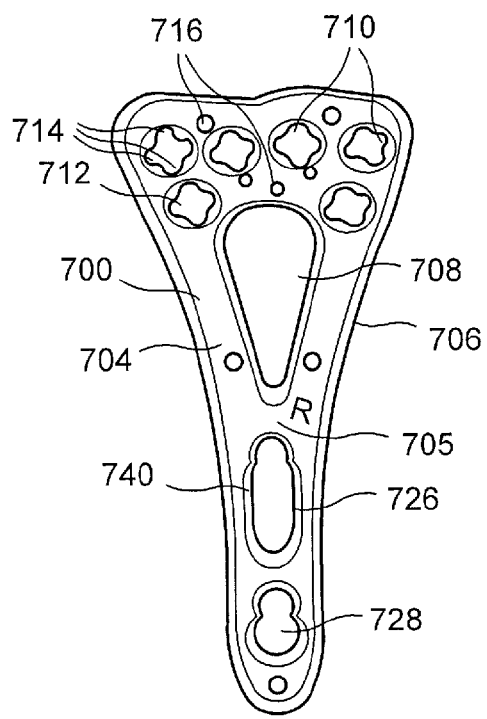
FIG. 10 depicts a bone plate according to a fifth alternate embodiment of the present invention.

As shown in FIG. 10, a bone plate 700 according to another embodiment of the present invention includes a substantially triangular end similar to the plates depicted in the earlier embodiments with a longitudinal extension 740 extending from a second end 705 of second and third walls 704, 706 configured to extend along a shaft of the bone. In addition, a first wall of the bone plate 700 comprises a plurality of variable angle screw holes—i.e., screw holes which permit a user to insert a screw therethrough at any desired angle relative to an axis of the screw hole (within a permitted range of angulation). Specifically, the first wall includes a first row of variable angle screw holes including four screw holes 710 longitudinally offset from one another and a second row having two screw variable angle holes 710 adjacent to right and left lateral walls thereof. It is noted, however, that the number and arrangement of the screw holes 710 may be varied without deviating from the spirit and scope of the present invention and that any combination of fixed angle and variable angle holes may be included as desired. As would be understood by those skilled in the art, each of the variable angle holes 710 includes a central opening 712 a diameter of which is selected to engage a head of a variable angle screw to be inserted therein with a plurality of outer bores 714 (in this case four outer bores 714) extending through the plate and spaced from one another about a circumference of the central opening 712. Each of the outer bores 714 opens into the central opening 712 so that a wall of the central opening 712 is discontinuous about the circumference thereof. As would be understood by those skilled in the art, the wall of the central opening includes a threading or a series of ridges designed to engage corresponding features on the head of the screw to be inserted therethrough to lock each screw in a corresponding one of the holes 710 at a desired angle relative to a central axis of the central opening 712. The central opening 712 has a profile along the central axis that is substantially hour glass shaped. That is, the central opening 712 extends into the plate from a proximal surface which faces away from the bone to a bone facing surface and has a diameter which tapers along the axis of the central axis from a maximum at the proximal surface to a minimum at a central portion configured to engage the head of a screw and then flaring outward to an opening at the bone facing surface having a diameter greater than that in the central portion. The wall of the central opening 712 in the central portion and the threading thereon includes a gap at each of the locations at which an outer bore 714 opens thereinto. The flared bone facing opening of the central opening and the outer bores 714 permit the shaft of a bone screw inserted thereinto to be angulated relative to the central axis within a permissible range—e.g., up to 20 degrees as would be understood by those skilled in the art.

A plurality of K-wire holes 716 are provided to aid in temporarily positioning the bone plate 700 over a bone. A window extending through the bone plate 700 is substantially teardrop shaped and reduced in width toward the second end 705. The longitudinal extension 740 comprises a first combination hole 726 and a second combination hole 728 in longitudinal alignment with one another. The first combination hole 726 in this embodiment is formed substantially similarly to the combination hole 126 while the second combination hole has two substantially circular portions open to one another, as those skilled in the art will understand. An outer profile of the variable angle locking compression bone plate 700 may be especially useful for the fixation of long bones or bones with multiple fracture sites.

Figure 11:
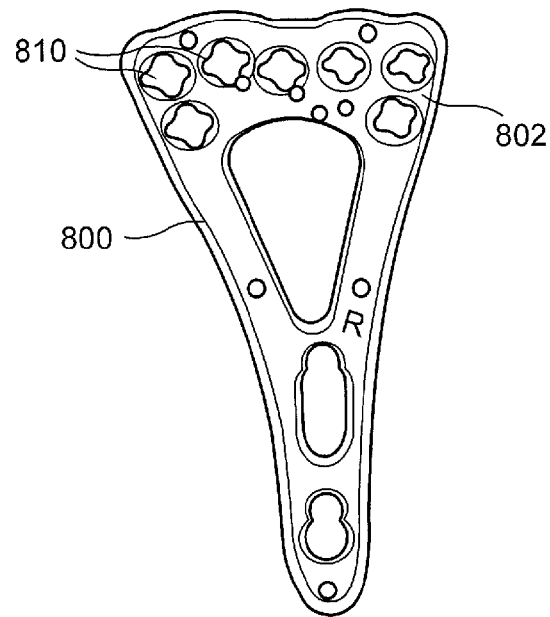
FIG. 11 depicts a bone plate according to a sixth alternate embodiment of the present invention.
Figure 12:
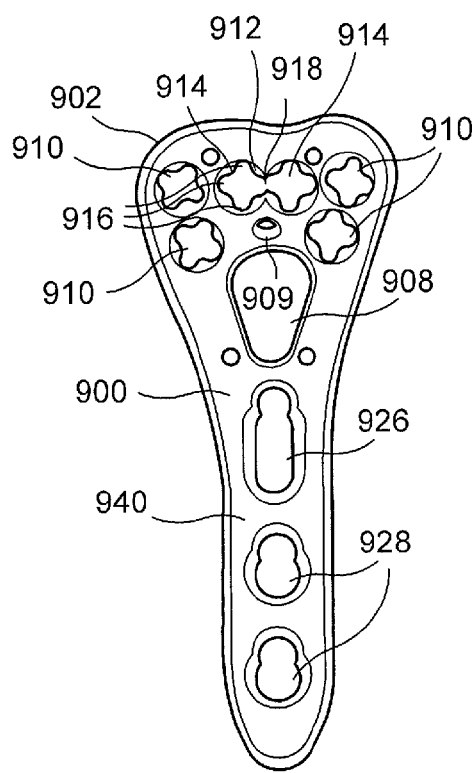
FIG. 12 depicts a bone plate according to a seventh alternate embodiment of the present invention.
Figure 13:
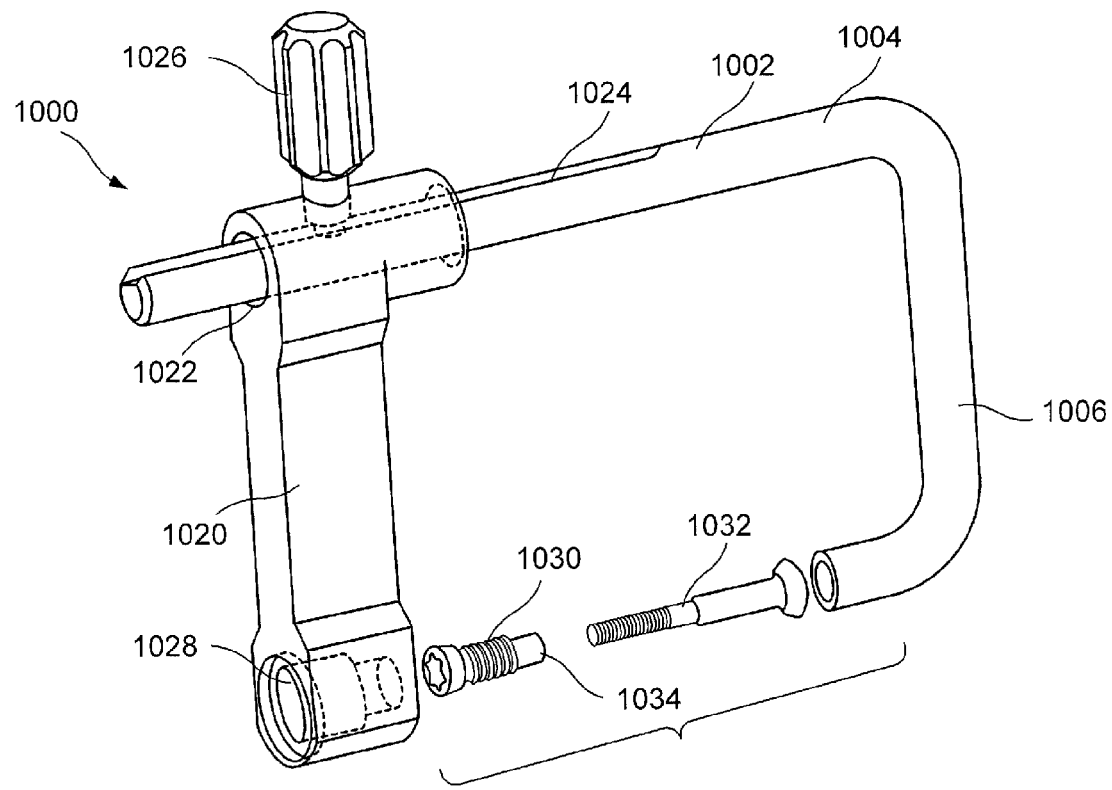
FIG. 13 depicts an aiming arm according to an eighth alternate embodiment of the present invention.

As shown in FIG. 11, a bone plate 800 includes seven variable angle screw holes 810 in a first wall 802 but is otherwise constructed similarly to the plate 700 described above. As shown in FIG. 12, a bone plate 900 according to yet another embodiment of the present invention is substantially similar to the bone plate 700 of FIG. 10 except that the first wall 902 thereof includes, in addition to the variable angle holes 910 similar to those of the plate 700, a variable angle combination hole 912 including two variable angle holes adjacent to one another and which are open to one another. The variable angle combination hole 912 includes two central openings 914 side by side with central axes of each of these openings 914 separated from one another by a distance less than a diameter of the openings 914 at a proximal surface of the plate 900 (i.e., a surface which faces away from the bone) so that the proximal ends of the openings 914 intersect with one another. In addition, each of the central openings 914 is surrounded by three outer bores 916 with the position which would be taken by an equally spaced fourth outer bore 916 being the location of a gap 918 opening the two central openings 914 to each other. The gap 918 is preferably no wider than the openings in the wall of the central openings 914 formed by each of the outer bores 916. Thus, the gap 918 does not decrease the extent of the threaded walls of the central openings 914 available to engage the heads of bone screws inserted thereinto. Furthermore, in addition to an elliptical combination hole 926, a longitudinal extension 940 of the bone plate 900 also comprises two substantially circular combination holes 928. The bone plate 900 is configured to be substantially symmetrical along a longitudinal centerline LC thereof. The bone plate 900 also comprises a window 908 formed substantially similarly as the window 108 of FIG. 1 with the exception of a substantially circular additional opening 909 provided on the first wall 902, the opening 909 being positioned adjacent to and being open to the window 908. The opening 909 also extends through the bone plate 900 from the first surface facing away from the bone to a bone facing surface thereof.

FIGS. 13-16 depict an aiming device 1000 according to another exemplary embodiment of the invention. The aiming device 1000 is substantially similar to the aiming device 200 of FIGS. 4-5 with the exception of the details highlighted below. The aiming device 1000 comprises a substantially cylindrical hooked arm 1002, a longitudinal section 1004 and a hooked section 1006 configured to receive a cannulated targeting tip 1008 formed substantially similar to the pointed tip 208. Specifically, the cannulated targeting tip 1008 is formed as a substantially cylindrical element having a plurality of longitudinal grooves 1010 configured to aid in gripping and manipulation thereof by a physician or other user. The cannulated targeting tip 1008 comprises a longitudinal bore 1012 extending therethrough configured to align with a bore 1014 extending through the hooked section 1006 of the aiming arm 100. The cannulated targeting tip 1008 is configured to be detachable from the hooked arm 1006 to permit attachment of screws of different diameters thereto. Specifically, the cannulated targeting tip 1008 may optionally be removed and replaced with another pointed tip (not shown) configured to permit attachment to a bone fixation device (not shown) having a larger or smaller diameter than a bone fixation device 1032 or to permit insertion of a drill bit 1018 or other device therethrough. Similarly, the bore 1014 may be dimensioned as needed to permit insertion of the required drill bit 1018 therethrough, as discussed in greater detail hereafter. The cannulated targeting tip 1008 further comprises one or more barbs 1016 at a distal end thereof configured and dimensioned to apply a gripping force to an approximated midpoint of a radial styloid of the bone. As described in greater detail earlier, such a positioning of the aiming device 100 permits the bone plate 100 to be seated proximate to the Watershed Line of the bone 10 to prevent complications with sinews. The exemplary cannulated targeting tip 1008 of the present invention permits a physician or other user to insert the drill bit 1018 through the hooked section 1006 to drill a bore into the bone after the aiming device 1000 has been positioned thereover in a target alignment.

Similar to the device 200, the aiming device 1000 also comprises a handle 1020 having a first through-hole 1022 at a first end thereof configured to receive the longitudinal section 1004 of the arm 1002 therethrough, a portion of the longitudinal section 1004 comprising a track 1024 to permit slidable movement of the handle therealong. A tightening mechanism 1026 is provided on the first end of the handle 1020 to lock a position thereof relative to the arm 1002. A second end of the handle 1020 comprises a second through-hole 1028 configured to permit insertion of a first bone fixation device 1030 therethrough. The first bone fixation device 1030 is preferably configured and dimensioned for insertion through a screw hole 110 of the bone plate 100, as will be described in greater detail below.

In accordance with an exemplary method according to the invention, the bone plate 100 is positioned over the target portion of bone (not shown) using the aiming device 2000 as described in greater detail with respect to earlier embodiments. Once properly positioned, the tightening mechanism 1026 of the aiming device 1000 is tightened to lock a position thereof over the bone. In the locked position, the pointed tip 1016 is seated over the approximated midpoint of the styloid of the bone so that the bone pin 218 may be positioned through the screw hole 110 of the bone plate 100. K-wires may then be inserted through the K-wire holes 116 of the bone plate 100 to aid in temporarily fixing a desired position of the bone plate 100 over the target portion of bone. The bone screws 16 are then screwed into the screw holes 110, excluding the screw hole 110 engaging the pin 218.

Figure 14:
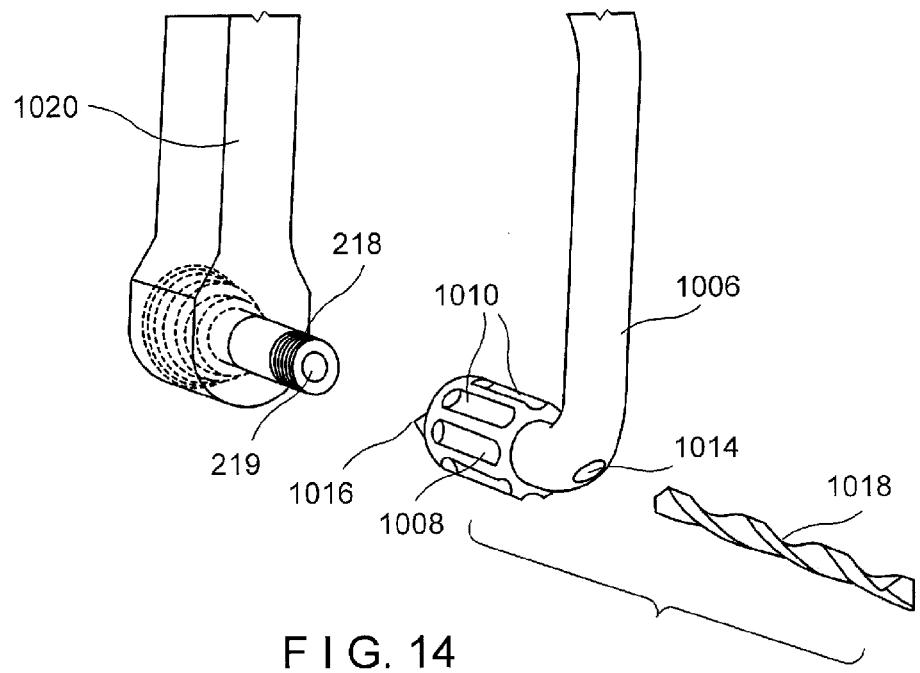
FIG. 14 depicts a zoomed view of the aiming arm of FIG. 13.
Figure 15:
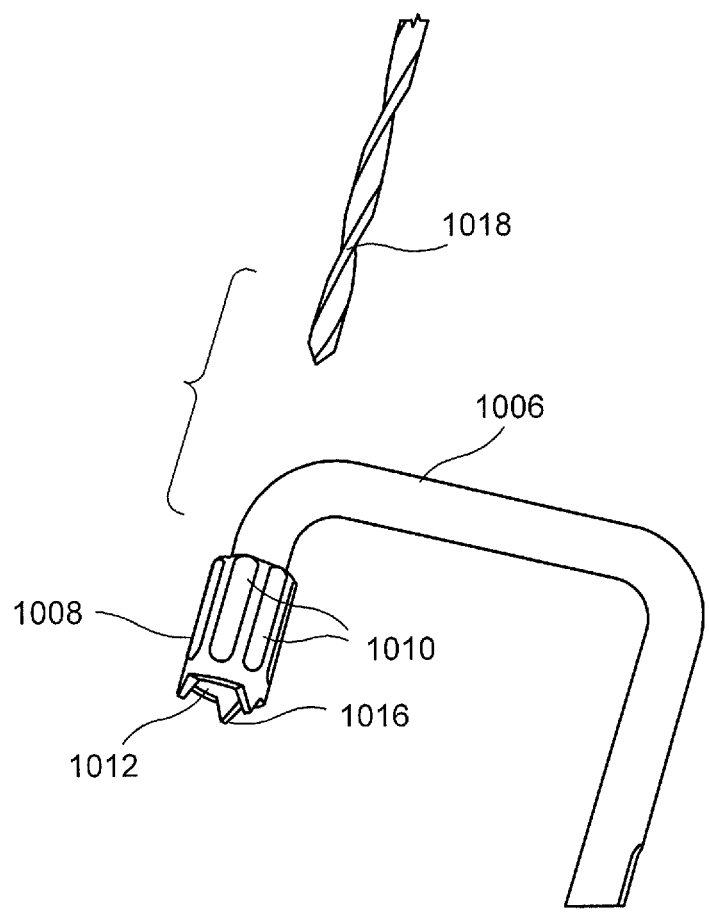
FIG. 15 depicts another zoomed view of the aiming arm of FIG. 13.
Figure 16:
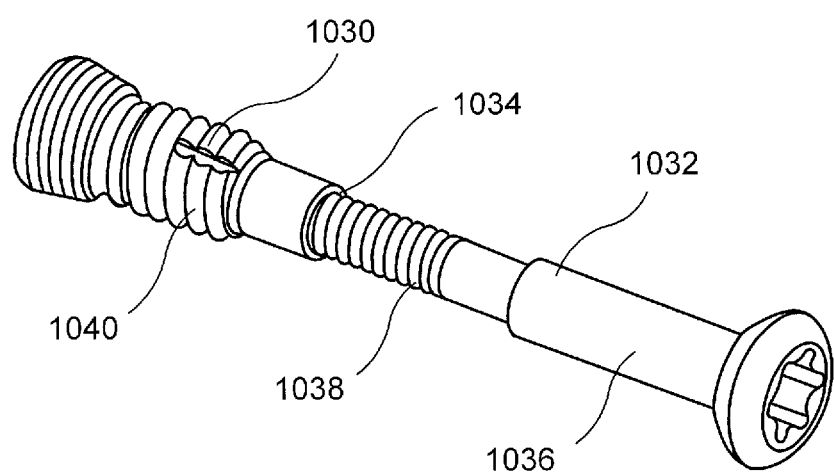
FIG. 16 depicts a perspective view of an exemplary bone fixation device for the aiming arm of FIG. 13.

A physician or other use may then insert the drill bit 1018 through the bore 1014 of the hooked portion 1006 to drill a bore that will meet the bore housing the pin 218. Specifically, as shown in FIG. 14, the bone pin 218 may comprise an opening 218 extending therethrough and configured to permit insertion of the drill bit 1018 therethrough. Thus, as the drill bit 1018 is advanced into the bone, a distal end thereof may extend into the opening 219 of the bone pin 218. Once the drill bit 1018 has been advanced to the target depth and all target bone screws have been inserted through the bone plate 100, the bone pin 218 and the drill bit 1018 are removed from the bone. The tightening mechanism 1026 may then be released to permit removal of the aiming device 1000 from the bone. The first bone fixation device 1030 may then be inserted through the screw hole 110 of the bone plate 100. The second bone fixation device 1032 is subsequently inserted through the borehole drilled by the drill bit 1018 until a distal end thereof is threadedly received within an internal threaded cannula 1034 of the first bone fixation device 1030, as shown in FIG. 16. The cannula 1034 extends into a distal portion of the first bone fixation device 1030 by a depth selected such that the second bone fixation device 1032 may be screwed thereinto until a head thereof engages an outer surface of the styloid of the bone, as those skilled in the art will understand. In an exemplary embodiment according to the invention, the second bone fixation device 1032 comprises a smooth outer wall 1036 and a reduced diameter threaded portion 1038 configured to be received within the cannula 1034. In this embodiment, the second bone fixation device 1032 is locked against the bone by engagement of the threaded portion 1038 with internal threads of the cannula 1034. In another embodiment, however, any portion of an outer wall of the second bone fixation device 1032 may be threaded to increase a holding strength thereof within the bone. Similarly, the first bone fixation device 1030 is depicted with a discrete portion of threading 1040 on an outer wall thereof. It is further noted that any portion of the first bone fixation device 1030 may be provided with external threading without deviating from the scope of the invention.

It will be understood by those of skill in the art that the bone plates of the present invention may be provided with any of a plurality of other features without deviating from the scope of the present invention. Specifically, the bone plates may be provided with any number of indentations, curves or twists to aid in alignment with the bone. Furthermore, the bone plate and window are not limited to triangular shapes and may alternately be formed of any other ringed shape (e.g., square, rectangular, elliptical, etc.).

It will be apparent to those skilled in the art that various modifications and variations can be made in the structure and the methodology of the present invention, without departing from the spirit or the scope of the invention. Thus, it is intended that the present invention cover the modifications and variations of this invention provided that they come within the scope of the appended claims and their equivalents.

What is claimed is:

1. A bone fixation plate, comprising:
    a plate body extending from a first end to a second end, the first end being configured and dimensioned for placement over a shaft of a bone, the second end being configured and dimensioned for placement over an epiphysis of the bone, an outer width of the plate body increasing from the first end to the second end to substantially conform to dimensions of the bone;
    an opening extending through the plate from a first surface which, when the plate is mounted on the target bone in a desired orientation, faces away from the bone to a second surface, which when in the desired orientation, faces the bone, the opening being positioned so that, when the plate is mounted over a target portion of the bone, a fracture of the bone is visible therethrough to aid in alignment of the bone plate, wherein a first side and a second side of the opening extend parallel to respective lateral sides of the plate body from a distal end of the opening to a proximal end of the opening;
    first and second holes extending through the plate from the first surface to the second surface, each of the first and second holes being structured to lockingly engage a threaded head of a bone fixation device inserted thereinto; and
    a variable angle compression hole extending through the bone plate from the first surface to the second surface and comprising a first compression opening adjacent and open to a second compression opening,
    wherein the first compression opening is substantially circular and the second compression opening is substantially oval.

2. The bone fixation plate of claim 1, wherein a shape of the opening substantially matches an outer shape of a portion of the plate body surrounding the opening.

3. The bone fixation plate of claim 1, wherein an outer shape of a distal portion of the plate body surrounding the opening is substantially triangular.

4. The bone fixation plate of claim 1, wherein the plate body is configured and dimensioned for placement over a distal radius.

5. The bone fixation plate of claim 1, wherein the opening is defined by first and second lateral walls of the plate and a distal wall, a width of the first wall is substantially equal to that of the second wall.

6. The bone fixation plate of claim 1, wherein a distal portion of the plate body is substantially triangular.

7. The bone fixation plate of claim 6, further comprising an elongate shaft extending proximally from the distal portion of the plate body.

8. The bone fixation plate of claim 1, wherein the first and second holes are fixed angle holes, and wherein hole axes of the first and second holes, when projected from the second surface, do not intersect one another.

9. The bone fixation plate of claim 1, wherein the first and second holes are variable angle holes configured to lockingly engage a threaded head of a bone fixation device inserted thereinto at any user selected angle relative to a hole axis of the corresponding one of the first and second variable angle holes within a permitted range of angulation.

10. The bone fixation plate of claim 9, wherein the first variable angle hole is formed as a central bore intersected by a plurality of peripheral bores opening into the central bore.

11. The bone fixation plate of claim 1, further comprising a wire hole extending through the plate body configured and dimensioned to receive a Kirschner wire therethrough.

12. The bone fixation plate of claim 8, wherein the first and second fixed angle holes extend through a distal wall of the plate body.

13. The bone fixation device of claim 1, wherein the first hole is distal of the second hole.

14. The bone fixation plate of claim 3, further comprising a threaded locking hole at a proximal end of the distal portion of the plate body.

15. The bone fixation plate of claim 1, wherein the opening further comprises a partially circular indentation extending distally thereinto, the indentation being configured to receive a portion of a bone fixation device therethrough.

16. A bone fixation system, comprising:

a bone fixation plate having a plate body extending from a first end configured and dimensioned for placement over a shaft of a bone to a second end configured and dimensioned for placement over an epiphysis of the bone, an outer diameter of the plate body increasing from the first end to the second end to substantially conform to dimensions of the bone, an opening extending through the plate from a first surface which, when the plate is mounted on the target bone in a desired orientation, faces away from the bone to a second surface, which when in the desired orientation, faces the bone, the opening being positioned so that, when the plate is mounted over a target portion of the bone, a fracture of the bone is visible therethrough to aid in alignment of the bone plate, and first and second holes extending through the plate from the first surface to the second surface, each of the first and second holes being structured to lockingly engage a threaded head of a bone fixation device inserted thereinto, wherein a first side and a second side of the opening extend parallel to respective lateral sides of the plate body from a distal end of the opening to a proximal end of the opening; and an aiming device having a hooked arm and a handle, the hooked arm being configured as an elongated element with a pointed tip at a distal end configured and dimensioned to contact an outer portion of the target bone, the handle being slidably positionable along the elongated element and positioned adjacent the bone fixation plate so that a bone fixation device inserted through the handle aligns with one of the first and second holes of the bone fixation plate.

17. The bone fixation system of claim 16, further comprising a tightening mechanism on the handle configured to lock a position of the handle relative to an aiming arm.

18. The bone fixation system of claim 16, wherein the first and second holes are fixed angle holes, wherein a longitudinal axis of the second hole is configured to prevent intersection with a longitudinal axis of the first hole.

19. The bone fixation system of claim 16, wherein the first and second holes are variable angle holes.

20. The bone fixation system of claim 19, wherein the first and second variable angle holes are formed with respective central holes being surrounded by a plurality of outer bores open thereto.

21. The bone fixation system of claim 16, wherein the pointed tip and a portion of the distal end of the hooked arm comprise an opening extending therethrough and configured to permit insertion of a drill bit therethrough.

22. The bone fixation system of claim 21, wherein the pointed tip is removably attached to the hooked arm.

* * * * *